US009572730B2

United States Patent
Young et al.

(10) Patent No.: US 9,572,730 B2
(45) Date of Patent: Feb. 21, 2017

(54) FEMININE PRODUCT DISPENSING ASSEMBLY

(71) Applicants: Angela Young, Kingman, AZ (US); Rosalind Robinson, Kingman, AZ (US)

(72) Inventors: Angela Young, Kingman, AZ (US); Rosalind Robinson, Kingman, AZ (US)

(*) Notice: Subject to any disclaimer, the term of this patent is extended or adjusted under 35 U.S.C. 154(b) by 38 days.

(21) Appl. No.: 14/509,743

(22) Filed: Oct. 8, 2014

(65) Prior Publication Data

US 2016/0101001 A1 Apr. 14, 2016

(51) Int. Cl.
| | |
|---|---|
| G07F 11/00 | (2006.01) |
| A47F 1/00 | (2006.01) |
| A61F 13/551 | (2006.01) |
| B65F 1/14 | (2006.01) |
| B65F 1/02 | (2006.01) |
| B65F 1/16 | (2006.01) |

(52) U.S. Cl.
CPC ....... *A61F 13/5515* (2013.01); *A61F 13/5512* (2013.01); *B65F 1/02* (2013.01); *B65F 1/1607* (2013.01); *B65F 1/1646* (2013.01); *A61F 2013/55195* (2013.01); *B65F 2001/1676* (2013.01); *B65F 2240/164* (2013.01)

(58) Field of Classification Search
CPC .............. A61F 13/5515; A61F 13/5512; A61F 2013/55195; B65F 1/00; B65F 1/1607; B65F 1/02; B65F 1/1646; B65F 2001/1676; B65F 2240/164
USPC ........................................................ 221/102
See application file for complete search history.

(56) References Cited

U.S. PATENT DOCUMENTS

| | | | | |
|---|---|---|---|---|
| 2,740,551 | A * | 4/1956 | Carew ..................... | A47F 1/085 221/34 |
| 3,543,918 | A * | 12/1970 | Borden .................. | B65D 83/10 206/356 |
| 3,860,304 | A | 1/1975 | Bolton | |
| 4,308,974 | A * | 1/1982 | Jones ..................... | A61F 15/001 221/196 |
| 4,706,845 | A | 11/1987 | Schnurer et al. | |
| 4,750,640 | A * | 6/1988 | Kobeck .................. | A47K 10/44 221/186 |
| 5,147,055 | A * | 9/1992 | Samson ................ | B65F 1/1615 220/252 |
| 5,638,957 | A * | 6/1997 | Brasier ................. | A61F 13/551 206/581 |
| 5,678,727 | A * | 10/1997 | Rice ......................... | A47F 1/06 221/102 |
| 6,152,079 | A * | 11/2000 | Chandler ................ | B65F 1/141 119/161 |
| D472,398 | S | 4/2003 | Sparkowski | |
| 6,540,103 | B2 | 4/2003 | Silvers | |
| 6,799,695 | B1 | 10/2004 | Borrero | |

(Continued)

FOREIGN PATENT DOCUMENTS

WO    WO2009108119    9/2009

*Primary Examiner* — Rakesh Kumar

(57) ABSTRACT

A feminine product dispensing assembly for containing and dispensing feminine products includes a canister structured to insertably receive a used feminine product. A pair of dispensers is each coupled to the canister. The dispensers are structured to dispense a new feminine product. A first lid is coupled to the canister. The first lid has an aperture extending therethrough. The used feminine product is insertable through the aperture. A second lid is coupled to the canister. The second lid closes the canister.

1 Claim, 4 Drawing Sheets

(56) References Cited

U.S. PATENT DOCUMENTS

| | | | |
|---|---|---|---|
| D501,602 S * | 2/2005 | Karlsson | D3/255 |
| 7,146,785 B2 * | 12/2006 | Stravitz | B65B 9/15 |
| | | | 206/470 |
| 7,357,274 B2 * | 4/2008 | Hewett | A47K 10/424 |
| | | | 221/34 |
| 7,958,994 B2 | 6/2011 | Weinmann | |
| 9,181,028 B1 * | 11/2015 | Stravitz | B65F 1/06 |
| 2007/0131716 A1 * | 6/2007 | Prabucki | B67D 1/0869 |
| | | | 222/146.6 |
| 2013/0228589 A1 | 9/2013 | Nickerson | |

* cited by examiner

FEMININE PRODUCT DISPENSING ASSEMBLY

BACKGROUND OF THE DISCLOSURE

Field of the Disclosure

The disclosure relates to dispensing devices and more particularly pertains to a new dispensing device for containing and dispensing feminine products.

SUMMARY OF THE DISCLOSURE

An embodiment of the disclosure meets the needs presented above by generally comprising a canister structured to insertably receive a used feminine product. A pair of dispensers is each coupled to the canister. The dispensers are structured to dispense a new feminine product. A first lid is coupled to the canister. The first lid has an aperture extending therethrough. The used feminine product is insertable through the aperture. A second lid is coupled to the canister. The second lid closes the canister.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
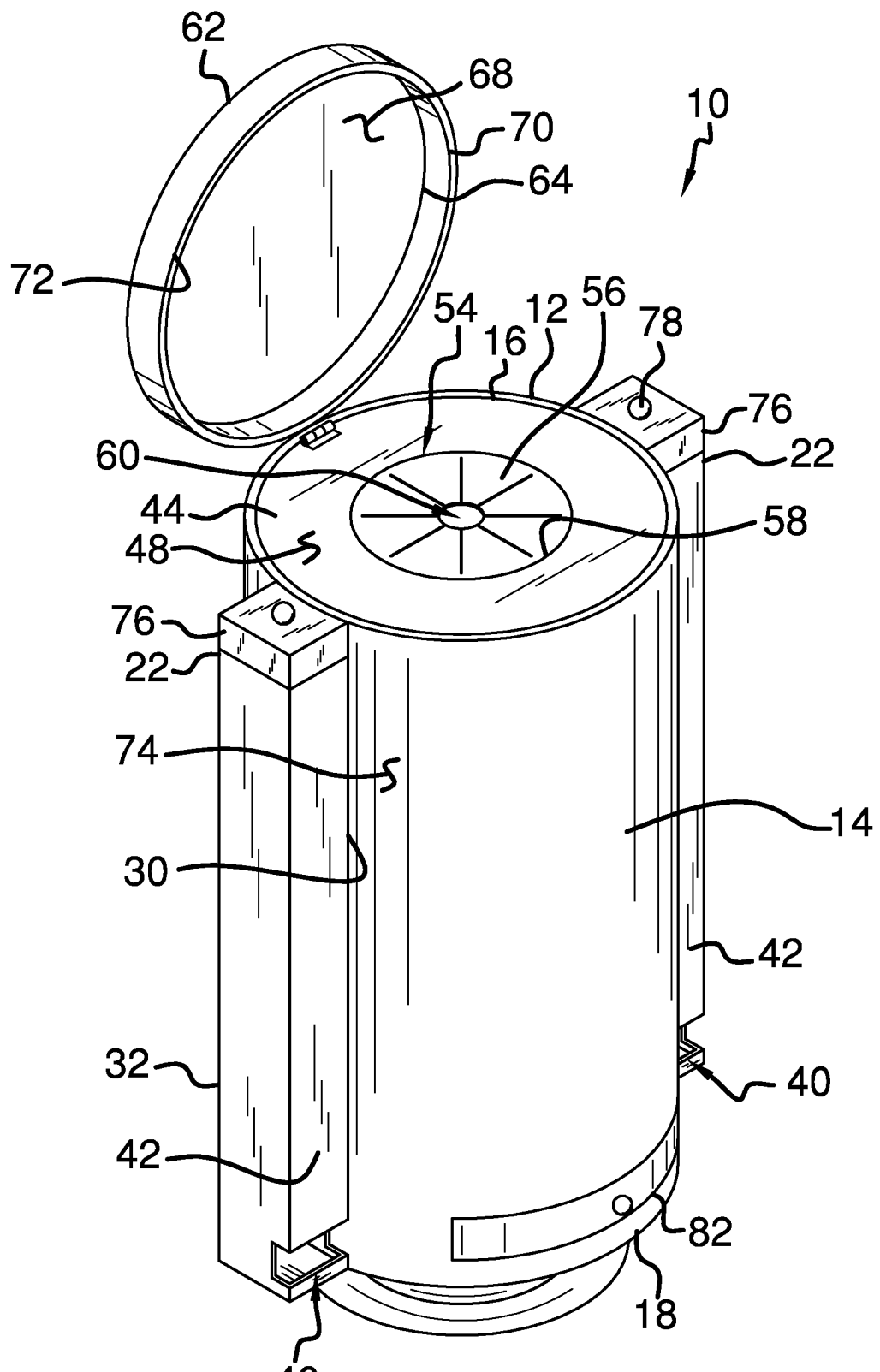
FIG. 1 is a perspective view of a feminine product dispensing assembly according to an embodiment of the disclosure.
Figure 3:
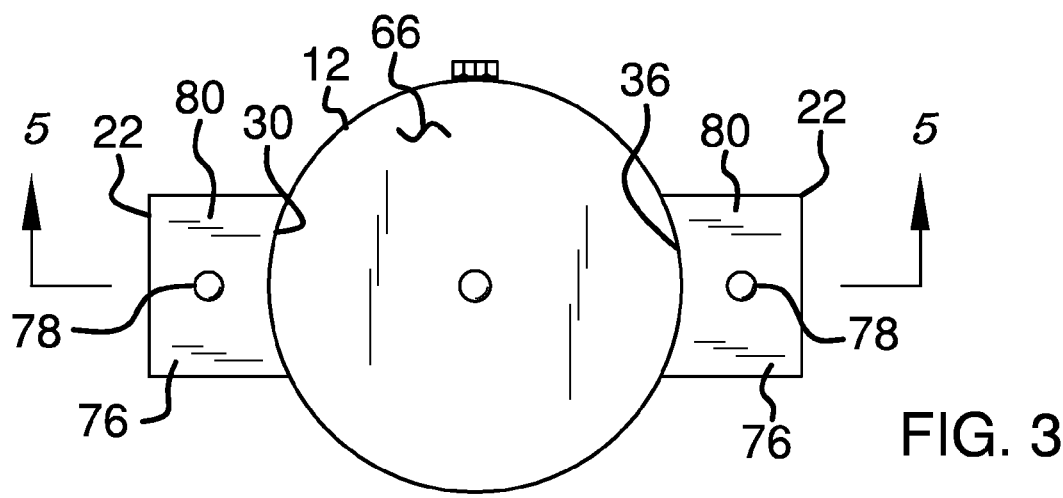
FIG. 3 is a top view of an embodiment of the disclosure.
Figure 2:
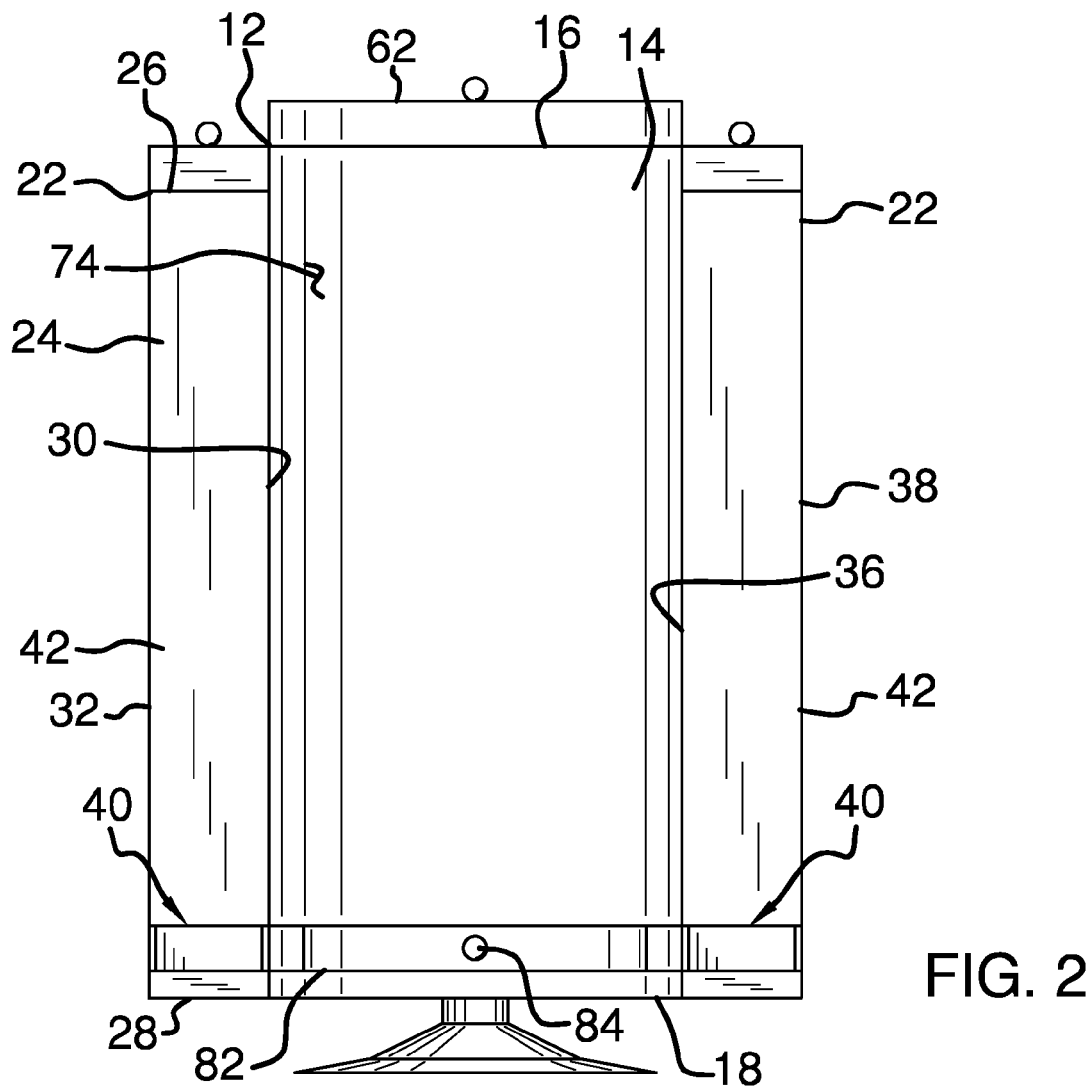
FIG. 2 is a front view of an embodiment of the disclosure.
Figure 4:
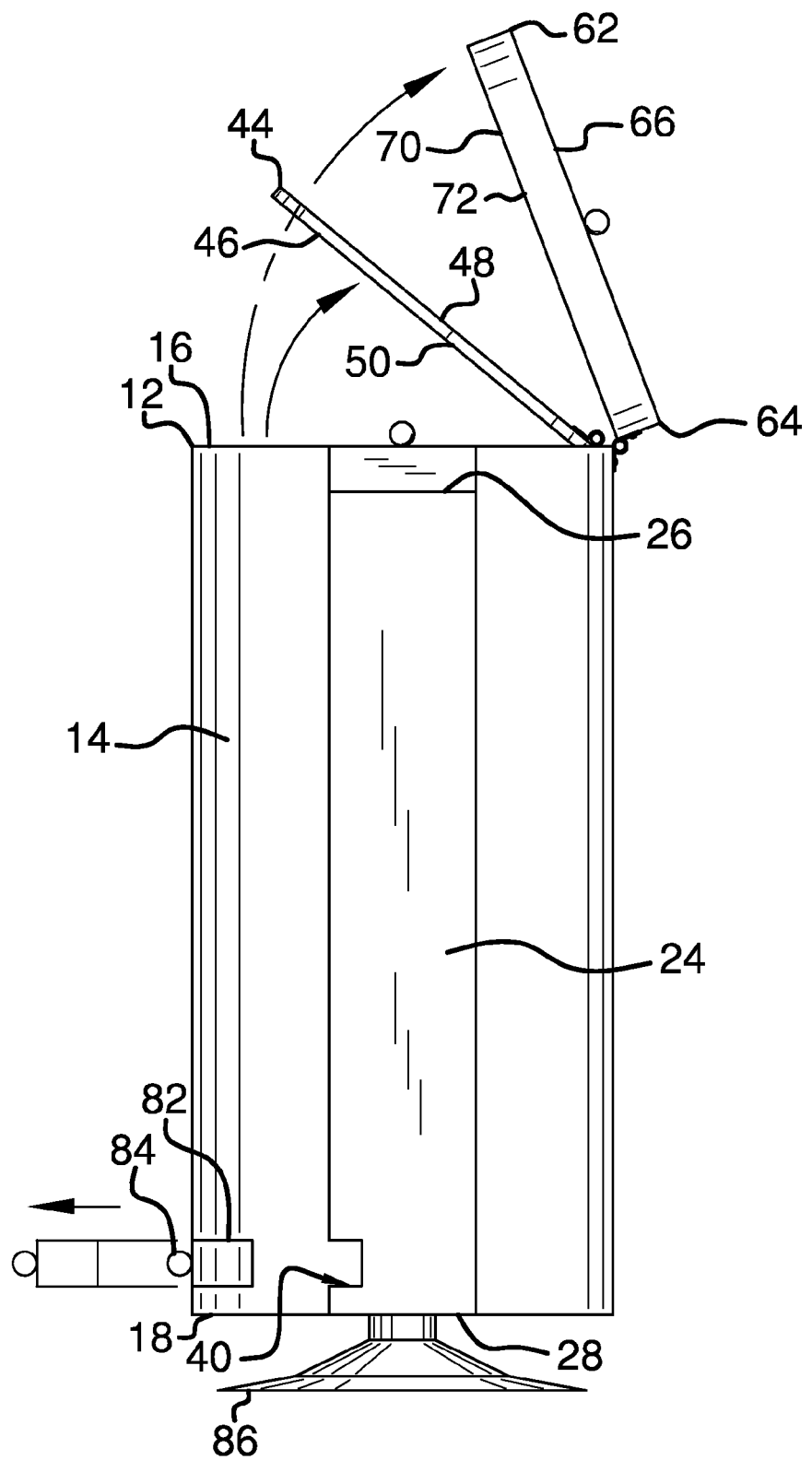
FIG. 4 is a right side view of an embodiment of the disclosure.
Figure 5:
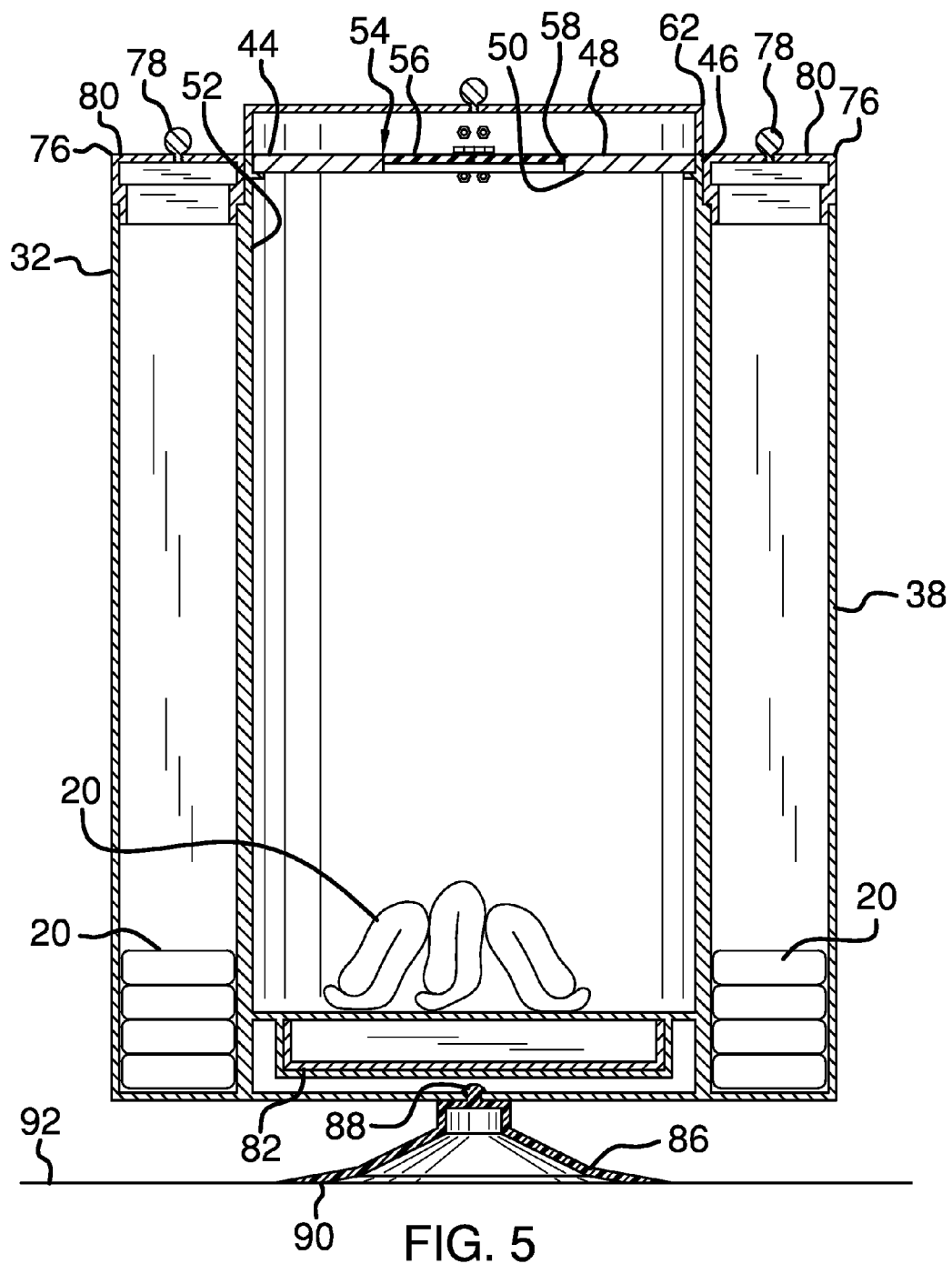
FIG. 5 is a cross sectional view taken along line 5-5 of FIG. 3 of an embodiment of the disclosure.

With reference now to the drawings, and in particular to FIGS. 1 through 5 thereof, a new dispensing device embodying the principles and concepts of an embodiment of the disclosure and generally designated by the reference numeral 10 will be described.

As best illustrated in FIGS. 1 through 5, the feminine product dispensing assembly 10 generally comprises a canister 12. The canister 12 has an outer wall 14 extending between each of a top end 16 and a bottom end 18 of the canister 12. The canister 12 is elongated between the top 16 and bottom 18 ends. The top end 16 of the canister 12 is open so the canister 12 is structured to insertably receive a used feminine product 20. The feminine product 20 may be a tampon or a maxi pad of any conventional design.

A pair of dispensers 22 is provided. The dispensers 22 each has an exterior wall 24 extending between an upper end 26 and a lower end 28 of the dispensers 22. Moreover, the dispensers 22 are elongated between the upper 26 and lower 28 ends. The upper end 26 of the dispensers 22 is open so the dispensers 22 are structured to contain new feminine products 20.

A first lateral side 30 of the exterior wall 24 of a first one 32 of the dispensers 22 is coupled to the outer wall 14 of the canister 12. The first dispenser 32 is coextensive with the outer wall 14 of the canister 12. A second lateral side 36 of the exterior wall 24 of a second one 38 of the dispensers 22 is coupled to the outer wall 14 of the canister 12. The second dispenser 38 is coextensive with the outer wall 14 of the canister 12. Additionally, the first 32 and second 38 dispensers are positioned on opposite sides of the outer wall 14 of the canister 12.

The exterior wall 24 of the first 32 and second 38 dispensers each has a slot 40 extending therethrough. The slots 40 are positioned on a forward side 42 of the exterior wall 24 of each of the dispensers 22. Additionally, the slots 40 are positioned proximate the lower end 28 of an associated one of the dispensers 22. The new feminine products 20 in each of the dispensers 22 is removable from the slots 40.

A first lid 44 is provided. The first lid 44 has an outer edge 46 extending between an upper surface 48 and a lower surface 50 of the first lid 44. The outer edge 46 of the first lid 44 is curvilinear so the first lid 44 has a disk shape. The outer edge 46 of the first lid 44 is hingedly coupled to an inside surface 52 of the outer wall 14 of the canister 12. Moreover, the first lid 44 is positioned proximate the top end 16 of the canister 12.

The first lid 44 has an aperture 54 extending through the upper 48 and lower 50 surfaces of the lid 44. The aperture 54 is centrally positioned on the first lid 44. A plurality of flaps 56 is coupled to a bounding edge 58 of the aperture 54. The flaps 56 are distributed around an entire circumference of the aperture 54. The flaps 56 extend inwardly toward a middle 60 of the aperture 54. Additionally, the flaps 56 may be comprised of a flexible material. The used feminine product 20 is insertable through the flaps 56 in the aperture 54.

A second lid 62 is provided. The second lid 62 has an extraneous edge 64 extending between each of an top surface 66 and a bottom surface 68 of the second lid 62. The extraneous edge 64 of the second lid 62 is curvilinear so the second lid 62 has a disk shape. A lip 70 is coupled to and extends downwardly from the extraneous edge 64 of the second lid 62. A lowermost edge 72 of the lip 70 is hingedly coupled to an outer surface 74 of the outer wall 14 of the canister 12. The second lid 62 is positioned proximate the top end 16 of the canister 12. The second lid 62 selectively closes the canister 12.

A pair of covers 76 is provided. Each of the covers 76 is removably positionable on the upper end 26 of an associated one of the dispensers 22. The covers 76 each close the associated one of the dispensers 22. A knob 78 is coupled to an uppermost side 80 of an associated one of the covers 76. The knobs 78 may be gripped.

A drawer 82 is provided. The drawer 82 is slidably coupled to the outer wall 14 of the canister 12. Additionally, the drawer 82 is positioned proximate the bottom end 18 of the canister 12. The drawer 82 is extendable outwardly from the canister 12 to remove the used feminine products 22 from the canister 12. A handle 84 is coupled to the drawer 82. The handle 84 may be gripped.

A base 86 has an uppermost end 88 and a lowermost end 90. The uppermost end 88 of base 86 may have a diameter that is less than a diameter of the lowermost end 90 of the base 86. The uppermost end 88 of the base 86 is coupled to the bottom end 18 of the canister 12. The lowermost end 90 of the base 86 abuts a support surface 92 so canister 12 is supported on the support surface 92. The support surface 92 may be a table top.

In use, the dispensers 22 are filled with the new feminine products 20. The canister 12 is emptied when the canister 12 becomes full of the used feminine products 20. The assembly 10 prevents an odor of the used feminine products 20 from escaping into the environment. Additionally, the assembly 10 keeps the used feminine products 20 discrete from other waste.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A feminine product dispensing assembly comprising:
    a canister, said canister having an outer wall extending between each of a top end and a bottom end of said canister, said canister being elongated between said top and bottom ends, said top end of said canister being open wherein said canister is structured to insertably receive a used feminine product;
    a pair of dispensers, said dispensers each having an exterior wall extending between an upper end and a lower end of said dispensers, said dispensers being elongated between said upper and lower ends, said upper end of said dispensers being open wherein said dispensers are structured to contain new feminine products;
    a first lateral side of said exterior wall of a first one of said dispensers being coupled to said outer wall of said canister such that said first dispenser is coextensive with said outer wall of said canister;
    a second lateral side of said exterior wall of a second one of said dispensers being coupled to said outer wall of said canister such that said second dispenser is coextensive with said outer wall of said canister;
    said first and second dispensers being positioned on opposite sides of said outer wall of said canister;
    said exterior wall of said first and second dispensers each having a slot extending therethrough, said slots being positioned proximate said lower end of an associated one of said dispensers such that the new feminine products in each of said dispensers is removable from said slots;
    a first lid, said first lid having an outer edge extending between an upper surface and a lower surface of said first lid, said outer edge of said first lid being curvilinear such that said first lid has a disk shape, said outer edge of said first lid being hingedly coupled to an inside surface of said outer wall of said canister such that said first lid is positioned proximate said top end of said canister
    said first lid having an aperture extending through said upper and lower surfaces of said lid such that said aperture is centrally positioned on said first lid, the used feminine product being insertable through said aperture;
    a second lid, said second lid having an extraneous edge extending between each of an top surface and a bottom surface of said second lid, said extraneous edge of said second lid being curvilinear such that said second lid has a disk shape;
    a lip coupled to and extending downwardly from said extraneous edge of said second lid, a lowermost edge of said lip being hingedly coupled to an outer surface of said outer wall of said canister such that said second lid is positioned proximate said top end of said canister, said second lid selectively closing said canister; and
    a base, said base having an uppermost end and a lowermost end, said uppermost end of said base being coupled to said bottom end of said canister, said lowermost end of said base abutting a support surface such that canister is supported on the support surface.

* * * * *